United States Patent [19]

Di Scipio

[11] Patent Number: 4,977,906
[45] Date of Patent: Dec. 18, 1990

[54] DIURNAL REHABILITATION FOR INCONTINENCE TRAINER

[76] Inventor: William J. Di Scipio, 64 Grove Ave., Larchmont, N.Y. 10538

[21] Appl. No.: 320,135

[22] Filed: Mar. 7, 1989

[51] Int. Cl.⁵ .......................... A61F 5/48; G08B 21/00
[52] U.S. Cl. ................................... 128/885; 128/886; 340/604
[58] Field of Search ............... 128/866, 885, DIG. 25; 604/361; 340/573, 602, 604, 603, 620

[56] References Cited

U.S. PATENT DOCUMENTS

| | | | |
|---|---|---|---|
| D. 259,864 | 7/1981 | Snyder | D10/116 |
| 2,687,721 | 8/1954 | Ellison | 128/138 |
| 2,866,454 | 12/1958 | McKenzie | 128/132 |
| 2,874,695 | 2/1959 | Vaniman | 128/138 |
| 3,460,123 | 8/1969 | Bass | 340/235 |
| 3,530,855 | 9/1970 | Balding | 128/866 |
| 3,678,928 | 7/1972 | Mozes | 128/866 |
| 3,759,246 | 9/1973 | Flack | 128/866 |
| 3,810,140 | 5/1974 | Finely | 340/235 |
| 4,106,001 | 8/1978 | Mahoney | 128/866 |
| 4,163,449 | 8/1979 | Regal | 128/138 A |
| 4,205,671 | 6/1980 | Lassen | 128/866 |
| 4,205,671 | 6/1980 | Lassen | 128/138 A |
| 4,212,295 | 7/1980 | Snyder | 128/138 A |
| 4,271,406 | 6/1981 | Wilson | 340/604 |
| 4,347,503 | 8/1982 | Uyehara | 340/604 |
| 4,539,559 | 9/1985 | Kelly | 128/866 |
| 4,592,018 | 5/1986 | Wiegman | 365/63 |
| 4,618,861 | 10/1986 | Gettens | 340/573 |
| 4,653,491 | 3/1987 | Okada | 128/866 |
| 4,659,314 | 4/1987 | Weinblatt | 340/573 |
| 4,754,264 | 8/1988 | Okada et al. | 340/573 |
| 4,760,383 | 7/1988 | DiLorenzo | 340/573 |

OTHER PUBLICATIONS

NYTONE ® Medical Prod., Inc., "NYTONE ® Enuretic Alarm", General Instructions & Information and Order Form.
Palco Labs, How to Use Wet-Stop.
Schmitt, "The Child Health Guide for Parents", (1986), excerpt.
Nite Train'R Enterprises, Inc., "Bedwetting Problem?", Sales brochure and instructions.
Wetbell ®, sales brochure and instructions.
Behavioral Research Technologies, Inc., "The DRI--TEK Enuresis Treatment Program".
StarChild/Labs., ". . . Introducing SleepDry ™ with 'Starry'", (1987).
StarChild/Labs., "How to Use Your SleepDry ™".
N. H. Eastwood & Son Ltd., "Mini Dri-Nite".
Sears, Roebuck & Co., Sales catalogue illustrating Lite-Alert ® Alarm and Wee-Alert Alarm.
Mountjoy et al., "Recent Technological Advancements in the Treatment of Enuresis", Behavior Modification, vol. 8, No. 3, Jul. 1984, pp. 291-315.

Primary Examiner—Robert A. Hafer
Assistant Examiner—Michael Brown
Attorney, Agent, or Firm—Pennie & Edmonds

[57] ABSTRACT

An apparatus for use in a diagnostic and biofeedback study and treatment of enuresis having an undergarment to be worn by the patient and sensors for detecting the presence of urine positioned thereon, a monitoring device with a time keeping component, a computer chip for recording the time of each detected enuresis incident, an alarm generating component having several operating modes and a power source component. Further, the apparatus has wires for electrically interconnecting the sensors and the monitoring device, and a clip for attaching the monitoring device to the undergarment.

19 Claims, 1 Drawing Sheet

DIURNAL REHABILITATION FOR INCONTINENCE TRAINER

TECHNICAL FIELD

The invention relates to a device to detect, record and signal the occurrence of enuresis and more particularly to a device used for diagnostic and biofeedback study and treatment for certain forms of urinary incontinence.

BACKGROUND ART

Various devices have been developed to sense the occurrence of nocturnal enuresis and to awaken the user upon detection of urine. Most of these devices are designed to be worn in the undergarments of the user. For example, see U.S. Pat. Nos. 2,687,721, 2,874,695, 3,460,123, 4,271,406, 4,653,491, 4,754,264 and 4,760,383. These devices are essentially signalling devices having an electrical circuit which is completed by the presence of urine thereby triggering an alarm.

U.S. Pat. No. 4,205,671 illustrates an enuresis sensor and a means for controlling the outflow. In addition to a sensor, this device is provided with means for supplying an electric shock to the nervous pudendus of the user thereby causing a contraction of a closing muscle in an attempt to prevent the discharge of urine.

A slightly different approach was taken in U.S. Pat. No. 3,810,140. Instead of activation of the alarm each and every time the user suffers enuresis, this device will only trigger the alarm 70 percent of the time. The object of this device is to provide an intermittent schedule of reinforcement instead of the continued reinforcement based on a theory of a lower relapse rate for users treated in this manner.

Similarly, U.S. Pat. No. 4,163,449 intends to "reward" the user for exercising control over enuresis. Upon initial detection of moisture, a noxious alarm is triggered. The alarm is terminated after a short period of time if the total amount of urine discharged is less than a given quantity, thereby rewarding the user.

Most of the prior art devices are designed for the treatment of primary nocturnal enuresis and do not consider prophylactic or symptom treatment or other forms of incontinence, including diurnal enuresis or combinations of physical and psychological causes of incontinence at all ages.

None of these prior art enuresis devices, however, utilize means for recording the events of wetting, to thereby develop a biofeedback training for the patient which can be used in combination with a signaling device for effectively assisting a wide range of patients in learning how to overcome the problem.

SUMMARY OF THE INVENTION

The present invention relates to an apparatus for use in a diagnostic and biofeedback study and treatment of patients suffering from enuresis. The Diurnal Rehabilitation for Incontinence (DRI) Trainer comprises an undergarment to be worn by the patient, means positioned upon this undergarment for detecting the presence of urine therein, a monitoring device having a time keeping component, a component operatively associated with the time keeping component for recording the time of each detection of urine, a power source component, means for electrically interconnecting the detecting means with the monitoring device components and means for attaching the monitoring device to the undergarment.

The undergarment used with this monitoring device may be any garment worn by the patient in the normal course of day or night activity. For example, this garment may be the patient's pants, diaper, pamper, or pajama pants. However, in the preferred embodiment, the device is used with a standard cotton polyester undergarment. The monitoring device is secured to the undergarment in the general proximity of the midline of the supra-pubic region of the patient. This placement is used to maximize the effective localization of the biofeedback signal near the bladder/sphincter region and to provide a convenient, concealed and secure location for continuous (24 hour) usage. The securing means is preferably a lightweight plastic or metallic clip which firmly engages the waistband of the undergarment.

Because the alarm signal will be timed in close temporal contiguity with the onset of urination (Less than 5 ccs of urine loss), the patient will not be subjected to wetting of the outer garment. Inhibition of the bladder contraction with a learned external voluntary sphincter muscle contraction forms the basis of the corrective biofeedback maneuver. Rapid detection also minimizes social embarrassment and the risk of urinary tract infections or skin excoriations developing secondary to the acidic or bacterial growth media provided by the presence of urine for extended periods of time.

Generally, the moisture detecting means are at least two elements which form an open circuit when located in close proximity to one another. Therefore, these means may be a pair of elements which are formed or coated with any suitable conductive material and which are electronically connected to the power source component. These elements may be easily and detachably mounted to the undergarment via clips or pins. In the preferred embodiment these elements are clips which grab the material of the garment. For example, the sensor clips may be joined together by "pinching" the outside of the undergarment in the region of the external urethral orifice. This placement avoids any metallic contact with the patient's skin and thereby guards against minor skin irritations secondary to the rough metallic clip. The pinching placement does not loose any efficiency in latency of detection of wetting.

Since the DRI Trainer is uniquely equipped with means for recording the time of each urine detection, it provides the clinician with the critical information for devising the desired biofeedback training. For example, the DRI Trainer provides the clinician with: (a) a means for arriving at differential diagnosis with regard to the physical/psychological etiologic component of the incontinence (neurogenic bladder disorders may have no relationship to environmental stressors, psychogenic incontinence shows otherwise); (b) a means for designing and implementing a biofeedback treatment regime through precisely timed measurement and recording of symptomatic/maladaptive behavior; (c) a means for objective and independent measurement of the patient's progress during biofeedback (or any other form of pre-post medical, pharmacological or surgical treatment of incontinence); and (d) a prophylactic or preventitive means of treating physical incontinence when changes of clothes are likely to be necessary on an extended or permanent basis.

An alternate embodiment of the invention relates to a DRI Trainer which also includes means which contact the patient for generating a signal to alert the patient and/or the clinician to an enuresis incident. The signal generating means is electrically connected to and operatively associated with the components of the monitoring device and the detecting means, and is used to generate an appropriate signal to attract the attention of the patient and/or the clinician. The most effective signals are sensory stimulations such as visual, audio or tactile stimulation, or any combination thereof. Preferably, the monitoring component has three selectable signalling modes: vibratory; auditory; and a combined vibratory/auditory mode.

In addition to a signalling means, the monitoring device may further include means for displaying the time of day and the appropriate alarm mode. There are numerous such displays available which are designed to represent time such as hands and lights, but the preferred displays are the light emitting diodes (LED) and liquid crystal display (LCD) types. Similarly, there are many such ways to represent the current alarm mode. For example, the monitoring device may be equipped with a switch having three positions, each corresponding to an alarm mode. Or, the device may have an alarm mode button which may vary in elevation from the face of the device according to the mode selected. Preferably, however, the display means will be provided with symbols which represent the various modes.

Located within the body of the monitoring device is means for recording and storing the time of each enuresis incident. Many such devices are available including encodeable magnetic tape or discs however, the preferred device is a memory chip similar to those found in standard handheld calculators. Advantageously, the computer chip should be operatively connected to a button or switch located on the display panel which resets or initializes the memory.

The power source component of the device is a battery and preferably a replaceable or rechargeable lithium battery having a 3 month to 1 year life. The battery should be sufficiently small to fit into the monitoring device in a readily accessible manner so as to render it easily removable. Also, the battery should produce sufficient voltage to power the unit and should be configured to prevent the danger of shock to the patient.

In another embodiment, the monitoring device is programmable such that it generates one of the above-described signals at pre-determined times. This embodiment allows the patient or clinician to program the device with time entries corresponding to periods of the patient's day which are frequently associated with enuresis incidents. As such, this feature would forewarn the patient and clinician allowing the patient to void prior to an occurrence, thereby eliminating corresponding discomfort and embarassment.

In yet another embodiment, the monitoring device is further provided with a remote signalling function which would relay silently to a caretaker or clinician by radio frequency signal the occurrence of an enuresis incident or time of day corresponding to frequent enuresis incidents. This feature is especially beneficial if the clinician does not remain in close proximity to the patient at all times, or if the patient is unable to respond to any signal for reason of a central nervous system deficit or temporary traumatic unconsciousness.

BRIEF DESCRIPTION OF THE DRAWINGS

The nature, advantages and various other additional features of the invention will appear more fully upon consideration of the illustrative embodiments now to be described in detail in connection with the accompanying drawing figures, wherein.

DETAILED DESCRIPTION OF THE PREFERRED EMBODIMENTS

Figure 1:
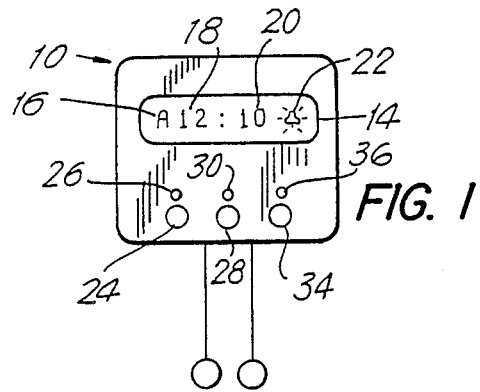
FIG. 1 is a front view of the apparatus of the present invention including sensory means, alarm, visual display and recording means.

The Diurnal Rehabilitation for Incontinence (DRI) Trainer according to the present invention is a biofeedback device used for diagnostic assessment and treatment of diurnal (daytime) urinary incontinence for children, adults and the elderly. In an auditory alarm mode, it may also be used for the effectively proven treatment of nocturnal enuresis (bedwetting). There is an extensive history of alarm devices for treatment of the latter condition, but none have been adapted to meet the needs of the patient who displays daytime enuresis.

Similar to the bedwetting alarm devices, the DRI Trainer is meant to sound an alarm at the earliest onset of urinary loss. However, differing from a night alarm, the DRI Trainer is programmable for silent alarms (vibration mode) so that the patient will not disturb or alert others. The presence of the silent alarm is also especially useful for the hearing impaired, such as the deaf and elderly. Another especially useful application of the device is during school hours when the child cannot interrupt a class by allowing an auditory signal and can instead use the silent alarm mode (self-control exercises are used as soon as the vibratory signal is perceived). Many children either do not use school bathrooms or school personnel are not readily available to cooperate with an intensive voiding program which can be alternatively guided by the alarm in the pre-set mode. The patient is thereby capable of wearing the alarm 24 hrs/day, depending upon the extent and nature of the incontinence problem.

In addition, the DRI Trainer is uniquely designed with a memory computer chip in order to record up to 50 events of wetting. Knowing the time and latency between enuretic events is critical for the clinician in arriving at an accurate diagnosis of the possible causes of the incontinence symptom. It also establishes a baseline for comparing progress in biofeedback training against the patient's own control levels. The close proximity of the DRI Trainer to the bladder/sphincter region on the body enhances the biofeedback training effect when the trainer is used for this purpose.

The DRI Trainer is also capable of emitting an auditory repeated beep sound alone or in combination with the vibrating signal. This enables the apparatus to be used for nocturnal enuresis as well as increases its effectiveness with patients who have need for multiple sensory input, such the mentally impaired, Alzheimer's Disease, multiple schlerosis, cerebral palsy, spinal cord birth defects or injury and other central nervous system (CNS) lesions.

In patients whose incontinence is neurogenic, or not amenable to improvement through biofeedback, surgical or other medical/pharmacologic treatment, the DRI Trainer is a useful prophylactic device which alerts either the patient or care takers to change undergarments because a wetting event has occurred. Avoidance of urine contaminated clothing for extended periods of time prevents the growth of bacteria and the adverse effects of bed sores, skin rashes and chronic urinary tract infections.

The battery of the DRI Trainer will not endanger the patient in any way, and is not capable of delivering aversive shock. The battery is replaceable and should last 3 months to 1 year depending upon intensity of use.

The primary function of the DRI Trainer is for the purpose of behavioral treatment of incontinence caused by problems such as unstable bladder syndrome, pseudoneurogenic or neurogenic bladder, bladder/sphincter dyssynergia, female urethral syndrome, secondary diurnal enuresis, and any form of enuresis secondary to CNS disturbances. The goal of treatment is to optimize the patient's own control of bladder functioning by raising the awareness of bladder sensation and correcting maladaptive bladder habits. The alarm amplifies or draws attention to the bladder contraction/sphincter relaxation mechanism of normal voiding and thereby allows the patient to gain greater central nervous system conscious control over the process. It is intended for use with supervised professional treatment only. The training is an alternative to irreversible surgical solutions or the iatrogenic effects of pharmacotherapy and is a treatment of choice where all other methods have failed. Biofeedback therapy usually lasts a minimum of 3 months and maximum of 1 year. There are no physical side effects and only time and commitment are required on the part of the patient and his/her family or caretaker.

Referring now to FIG. 1, there is illustrated the detector and function control unit 10 which is a chronograph/alarm capable of keeping and recording time having clip sensors 12 and 13, visual display panel 14, time advance button 24, time selection button 26 for setting the proper time of day, memory recall button 28, memory initialization button 30, alarm selection signal button 34 and programming button 36. Unit 10 is powered by a replaceable battery (not shown) having a life of 3 months to 1 year which presents no danger of electrical shock to the patient.

Operatively connected to the control unit 10 by lead wires are clip sensors 12, 13 which are formed or coated by a suitable conductive substance. When located in close proximating to one another, clip sensors 12, 13 comprise an open circuit which is completed by the presence of urine or moisture. In addition, the sensors 12, 13 include grasping means, such as a clip or a clamp, to provide a firm attachment to an undergarment. U.S. Pat. No. 2,687,721 illustrates one form of clip sensor which may be employed in the present invention.

Visual display panel 14 is operatively connected to a conventional internal time keeping apparatus (not shown). Many such timepieces are known by those skilled in the art of watchmaking including, but not limited to, a mechanical or electrical watch or clock capable of keeping accurate time. Such a timepiece may readily be designed or adapted to fit snuggly within the body of unit 10.

Display panel 14 may be any suitable visual display such as a light emitting diode (LED) or a liquid crystal display (LCD), but is preferably an LCD since this type of display is more energy efficient and more easily read in the daylight. Included within panel 14 are AM/PM indicator 16, hour indicator 18, minute indicator 20 and alarm mode indicator 22. As shown in FIG. 1, AM/PM indicator 16 displays the letter "A" representing AM hours. Similarly, indicator 16 will display the letter "P" for PM hours. Likewise, hour indicator 18 and minute indicator 20 numerically display the appropriate hour and minutes respectively.

Unit 10 is provided with an alarm which is operatively connected with clip sensors 12, 13 so that the alarm is triggered when the sensor detect the presence of moisture. The alarm is activated for a brief period, such as 30 seconds. The alarm may have a manual switch to terminate the alarm prior to the automatic shut off, or the alarm may also be deactivated before completion of the 30 second signal by unclasping the sensor. In either event, the unit will automatically record the time of the event and reset for the next incident.

In the preferred embodiment, unit 10 has three different alarm modes; a vibratory mode; an auditory mode; and a combined vibratory/auditory mode. When the alarm is triggered in the vibratory mode, unit 10 emits a steady vibration thereby producing a sensation which alerts the patient of the enuresis incidence. The intensity of the vibration may be adjustable up to a limit sufficient to wake a sleeping patient when used for nocturnal enuresis. This mode is especially effective for patients suffering from diurnal (daytime) urinary incontinence since it alerts only the patient, eliminating undue embarrassment. Triggering the alarm in the auditory mode causes unit 10 to emit a alerting noise, such as ringing, beeping, chirping, buzzing and the like which is capable awakening the patient and alerting a clinician. Unit 10 is preferably provided with means to adjust the volume of this alarm according to the needs of the patient, clinician and operating environment. When activated in the combined vibratory/auditory mode, the alarm causes unit 10 to simultaneously produce both of the above-described effects. This mode is particularly suited for use with patients who require multiple sensory input.

Alarm mode indicator 22 features three different icons corresponding to the appropriate alarm mode. For example, indicator 22 will display a bell to symbolize the auditory mode, a vibrator to symbolize the vibratory mode or both the bell and vibrator to illustrate the combined vibratory/auditory mode.

Function control unit 10 is provided with several pushbutton controls to select and set the various unit functions. Time advance button 24 is used in combination with time selection button 26 to set the time and alarm signal selection button 34 is used to choose the alarm mode. As way of illustration, time selection button 26 is used to select one of three variables to be set: AM/PM; the hour; or the minute; by successive pressings. For example, pressing button 26 once causes the AM/PM indicator 16 to blink. Press again, hour indicator 18 blinks, press again, minute indicator 20 blinks and finally pressing again returns display 14 to operating mode.

A blinking indicator signifies the ability to advance that icon to the next increment by pressing time advance button 24. Pressing time selection button 26 twice, for example, causes hour indicator 18 to blink, the hour can then be advanced by subsequent pressing of time advance button 24. Similarly, alarm signal selection button 34 can be sequentially pressed to choose the desired alarm mode.

Access to these buttons can be restricted in order to prevent accidental interference or intentional manipulation by recalcitrant patients. These buttons may, for example, be recessed into the body of unit 10 thereby requiring a pen or knife tip or some other suitably pointed object to maneuver them. Similarly, a simple keylock system can be implemented. Or, these buttons may be enclosed within a hinged cover which requires a key or sharp instrument to open. These features are optional: most patients are found to be cooperative because failures to respond to treatment or to improve in the control of urine discharge are not easily concealed.

Enclosed within control unit 10 is a memory computer chip, not shown, similar to those found in common handheld calculators. Such chips have constant memory and are capable of recording and storing a number of inputs. These chips are operatively connected to the internal time keeping apparatus and clip sensors 12, 13 so that each recorded incidence includes the time of the occurrence. The chip in the current invention is preferably capable of storing up to 50 enuresis incidents. In addition, unit 10 is provided with memory recall button 30 which, when consecutively pressed, sequentially recalls the time of each enuresis occurrence. The memory of the chip is reset to 0 by pressing memory initialization button 30. Programming button 36 is electronically and operative connected to the memory computer chip. Button 36 is used by the patent or clinician to store up to 15 pre-selected times corresponding to periods of the day which are frequently associated with enuresis incidents during which the alarm is to be automatically activated. This feature would forewarn the patient and clinician to the likelihood of an enuresis incident therefore allowing the patient to void.

Figure 2:
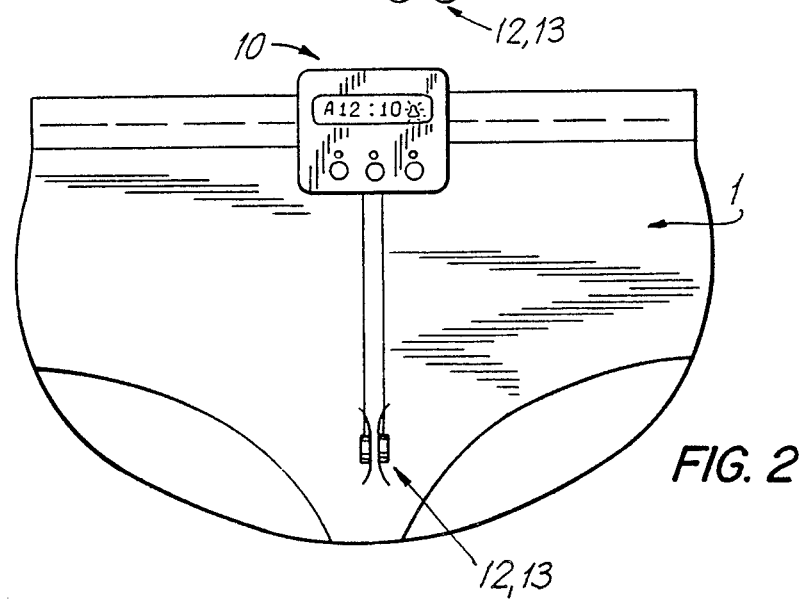
FIG. 2 illustrates the apparatus of FIG. 1 attached to the waistband of a typical undergarment.
Figure 4:
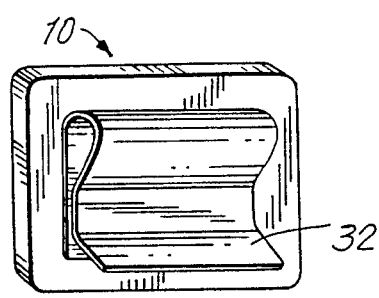
FIG. 4 is a rear perspective view of the apparatus of FIG. 1.
Figure 3:
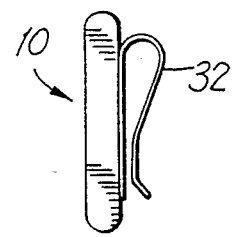
FIG. 3 is an end view of the apparatus of FIG. 1 detailing a clip for attachment to a waistband.

As shown in FIG. 2, control unit 10 may be used with any supportive clothing worn by the patient including a diaper, pamper or pajama pant, but is preferably secured to the waistband of a cotton undergarment 1 via attachment clip 32, shown in FIGS. 3 and 4. Clip sensors 12, 13 are easily secured to undergarment 1 in a close proximity to one another, either on the same or opposite sides of the garment material. These sensors should be located in the outside front or outside rear of the garment thereby corresponding with the region nearby the external urethral orifice of the patient. The sensor clips may be joined together by "pinching" the outside of the undergarment in the region of the external urethral orifice. This placement avoids any metallic contact with the patient's skin and thereby guards against minor skin irritations secondary to the rough metallic clip. The pinching placement does not loose any efficiency in latency of detection of wetting. Mounted as such, sensors 12, 13 present no discomfort or danger of electrical shock to the patient.

In operation, undergarment 1 is fitted such that sensors 12, 13 are positioned in close proximity to the bladder/sphincter region of the patient. During an enuresis incidence, moisture is absorbed by the cotton undergarment 1 in the region of sensors 12. When undergarment 1 is sufficiently wet, the open circuit across clip sensors 12, 13 is completed through the garment. Subsequently, the alarm, corresponding to the selected mode, activates for 30 seconds and the time of the occurrence is recorded by the memory chip.

It is possible to monitor the occurrences of urine discharge to determine when future occurrences are likely. This information can be used to help the patient learn when to properly void urine prior to such occurrences. The vibrational stimulation can be programmed to alert the patient at a predetermined time prior to the expected (or usual) occurrences so as to teach the patient how to avoid them.

While it is apparent that the invention herein disclosed is well calculated to fulfill the objects above stated, it will be appreciated that numerous embodiments and modifications may be devised by those skilled in the art, and it is intended that the appended claims cover all such modifications and embodiments as fall within the true spirit and scope of the present invention.

What is claimed is:

1. A self-contained, portable apparatus for use in a diagnostic and biofeedback study and treatment of urinary incontinence, comprising:
    an undergarment to be worn by the patient to be treated;
    means positioned upon said undergarment for detecting the presence of urine therein;
    a monitoring device comprising a time keeping component;
    a component operatively associated with said time keeping component for recording the time of each detection of the presence of urine by said detecting means;
    a power source component;
    means for electrically interconnecting said detecting means and said monitoring device components; and
    means for attaching said monitoring device to said undergarment; wherein the monitoring device further comprises means for generating a signal to apprise the patient of each detection of the presence of urine by the detecting means, said signal generating means electrically connected to and operatively associated with said monitoring device components and said detecting means, wherein said signal includes a vibratory mode, and auditory mode and a combination vibratory/auditory mode.

2. The apparatus of claim 1 wherein said signal generating means includes means for selecting one of said signal modes.

3. The apparatus of claim 2 wherein said monitoring device further comprises means for displaying time and said signal mode.

4. The apparatus of claim 3 wherein said displaying means is a light emitting diode.

5. The apparatus of claim 1 wherein said monitoring device further comprises means for generating said signal at predetermined times independent of the detection of the presence of urine by the detecting means.

6. The apparatus of claim 1 wherein said power source component is a battery.

7. The apparatus of claim 1 wherein said detecting means comprise a pair of clips formed or coated with a conductive material and electronically connected to said power source component.

8. The apparatus of claim 1 wherein said monitoring device further comprises means for re-setting the recording component.

9. The apparatus of claim 1 wherein said recording component is a memory computer chip capable of recording the time of as many as 50 detections of urinary incontinence events.

10. A self-contained, portable apparatus for use in a diagnostic and biofeedback study and treatment of urinary incontinence comprising:
    an undergarment to be worn by the patient to be treated;

means positioned upon said undergarment for detecting the presence of urine therein;

a monitoring device comprising a time keeping component;

a component operatively associated with said time keeping component for recording the time of each detection of the presence of urine by said detecting means;

a component contacting said patient for generating a non-auditory signal including a vibratory mode to apprise the patient of each detection of the presence of urine by the detecting means;

a power source component;

means for electrically interconnecting said detecting means and said monitoring device components; and means for attaching said monitoring device to said undergarment.

11. The apparatus of claim 10 wherein the monitoring device further comprises means for generating an auditory signal to apprise the patient of each detection of the presence of urine by the detecting means.

12. The apparatus of claim 11 wherein the monitoring device further comprises means for displaying time and indicating the type of signal to be generated.

13. The apparatus of claim 12 wherein said displaying means is a light emitting diode.

14. The apparatus of claim 10 wherein said power source component is a battery.

15. The apparatus of claim 10 wherein said electronic sensory means comprise a pair of clips formed or coated with a conductive material and electronically connected to said power source component.

16. A self-contained, portable apparatus for use in a diagnostic and biofeedback study and treatment of urinary incontinence, comprising:

an undergarment to be worn by the patient to be treated;

means positioned upon said undergarment for detecting the presence of urine therein;

a monitoring device comprising a time keeping component;

a component operatively associated with said time keeping component for recording the time of each detection of the presence of urine by said detecting means;

an alarm generating component having several operating modes, wherein said modes include a vibratory mode, an auditory mode and a combination vibratory/auditory mode for apprising the patient of each detection the presence of urine by the detecting means;

a power source component;

means for electrically interconnecting said detecting means and said monitoring device components; and means for attaching said monitoring device to said undergarment.

17. The apparatus of claim 16 wherein said monitoring device further comprises means for selecting one of said alarm modes and means for displaying time and the alarm mode selected.

18. The apparatus of claim 17 wherein said displaying means is a light emitting diode.

19. The apparatus of claim 16 further comprising programming means electrically connected to said time keeping component and said alarm generating component for preselecting up to 15 activations of said alarm.

* * * * *